United States Patent
Hanawa et al.

(10) Patent No.: US 11,692,244 B2
(45) Date of Patent: Jul. 4, 2023

(54) ALLOY FOR BIOMEDICAL USE AND MEDICAL PRODUCT

(71) Applicants: TOKUSEN KOGYO CO., LTD., Ono (JP); NATIONAL UNIVERSITY CORPORATION TOKYO MEDICAL AND DENTAL UNIVERSITY, Tokyo (JP)

(72) Inventors: Takao Hanawa, Tokyo (JP); Yusuke Tsutsumi, Tokyo (JP); Mitsutaka Sasakura, Ono (JP)

(73) Assignees: TOKUSEN KOGYO CO., LTD., Hyogo (JP); National University Corporation Tokyo Medical and Dental University, Tokyo (JP)

( * ) Notice: Subject to any disclaimer, the term of this patent is extended or adjusted under 35 U.S.C. 154(b) by 619 days.

(21) Appl. No.: 16/634,921

(22) PCT Filed: Jul. 24, 2018

(86) PCT No.: PCT/JP2018/027725
§ 371 (c)(1),
(2) Date: Jan. 29, 2020

(87) PCT Pub. No.: WO2019/035324
PCT Pub. Date: Feb. 21, 2019

(65) Prior Publication Data
US 2020/0157660 A1   May 21, 2020

(30) Foreign Application Priority Data
Aug. 18, 2017  (JP) ................................. 2017-158222

(51) Int. Cl.
*C22C 16/00*   (2006.01)
*A61B 17/80*   (2006.01)
*A61B 17/86*   (2006.01)
*A61F 2/30*   (2006.01)
*C22F 1/18*   (2006.01)

(52) U.S. Cl.
CPC .............. *C22C 16/00* (2013.01); *A61B 17/80* (2013.01); *A61B 17/86* (2013.01); *A61F 2/30* (2013.01); *C22F 1/186* (2013.01)

(58) Field of Classification Search
CPC .................................. C22F 1/186; C22C 16/00
See application file for complete search history.

(56) References Cited

U.S. PATENT DOCUMENTS

| | | | | |
|---|---|---|---|---|
| 3,261,682 A | * | 7/1966 | Rosler | ..................... C22C 16/00 376/457 |
| 4,040,129 A | * | 8/1977 | Steinemann | ........... A61B 17/72 606/76 |
| 2019/0201576 A1 | | 7/2019 | Hanawa et al. | |

FOREIGN PATENT DOCUMENTS

| CN | 101569763 A | 11/2009 |
|---|---|---|
| JP | 2006-183100 A | 7/2006 |
| JP | 2006-183104 A | 7/2006 |
| JP | 2010-075413 A | 4/2010 |
| WO | 2018/047611 A1 | 3/2018 |

OTHER PUBLICATIONS

International Search Report for PCT/JP2018/027725 dated Feb. 21, 2019 (PCT/ISA/210).

* cited by examiner

*Primary Examiner* — Jessee R Roe
(74) *Attorney, Agent, or Firm* — Sughrue Mion, PLLC

(57) ABSTRACT

An alloy for biomedical use includes Zr as a main component, Nb the content of which is not less than 0.1% by weight and not greater than 25% by weight, Mo the content of which is not less than 0.1% by weight and not greater than 25% by weight, and Ta the content of which is not less than 0.1% by weight and not greater than 25% by weight. A tensile strength of the alloy is not less than 1000 MPa. A total content of Nb, Mo, and Ta in the alloy is not less than 2% by weight and not greater than 50% by weight. Mass susceptibility of the alloy is not greater than $1.50 \times 10^{-6}$ cm$^3$/g. A Young's modulus of the alloy is not greater than 100 GPa. Also disclosed is a medical product including the alloy and a method for producing the alloy.

12 Claims, 5 Drawing Sheets

ALLOY FOR BIOMEDICAL USE AND MEDICAL PRODUCT

CROSS REFERENCE TO RELATED APPLICATIONS

This application is a National Stage of International Application No. PCT/JP2018/027725 filed Jul. 24, 2018, claiming priority based on Japanese Patent Application No. 2017-158222 filed Aug. 18, 2017.

TECHNICAL FIELD

The present invention relates to medical products such as biomedical implants and medical devices, and alloys suitable for these medical products.

BACKGROUND ART

A patient who has, for example, a partially defective skull, cheek bone, or jaw bone is treated by using an artificial bone. An artificial bone is implanted in an organism to fill the defective portion. A patient who lost her/his tooth is treated by using an artificial tooth root. The artificial tooth root is implanted in a jaw bone. The artificial bone and the artificial tooth root are each called an implant. In addition to the implant, a cerebral artery clip, an artificial heart valve, an intravascular stent, a fixation plate for a broken bone, and the like are implanted in organisms.

When diagnostic imaging is performed for a patient who has such a biomedical implant in his/her body by using a magnetic resonance imaging (MRI) device, a false image called an artifact may occur near the biomedical implant in the image. The artifact degrades the accuracy for the diagnostic imaging.

For MRI diagnosis, various medical devices are used. The artifact in the image may be caused by the medical device. Such an artifact also degrades accuracy for diagnostic imaging.

The artifact is caused by a strong magnetic field during MRI diagnosis. When a material having low magnetic susceptibility is used for medical products such as biomedical implants and medical devices, the artifact can be reduced. An alloy, for biomedical use, which contains Zr, and a main transition metal other than Zr is disclosed in JP2010-75413. Specifically, an alloy in which the content of Nb is not less than 3% by weight and not greater than 12% by weight and the remainder is Zr, is disclosed in this publication. This alloy has low magnetic susceptibility, whereby the alloy can allow reduction of an artifact.

CITATION LIST

Patent Literature

Patent Literature 1: JP2010-75413

SUMMARY OF THE INVENTION

Problems to be Solved by the Invention

The mechanical characteristics of the alloy disclosed in JP2010-75413 are not sufficient. An object of the present invention is to provide an alloy, for biomedical use, which has low magnetic susceptibility and excellent mechanical characteristics, and to provide a medical product using the alloy.

Solution to the Problems

An alloy for biomedical use according to the present invention includes Zr as a main component, Nb the content of which is not less than 0.1% by weight and not greater than 25% by weight, Mo the content of which is not less than 0.1% by weight and not greater than 25% by weight, and Ta the content of which is not less than 0.1% by weight and not greater than 25% by weight. A tensile strength of the alloy is not less than 1000 MPa.

Preferably, a total content of Nb, Mo, and Ta in the alloy is not less than 2% by weight and not greater than 50% by weight.

Preferably, a ratio (PMo/PTa) of a content PTa (% by weight) of Ta to a content PMo (% by weight) of Mo in the alloy is not less than 1/20 and not greater than 1/3.

Preferably, a 0.2% proof stress of the alloy is not less than 900 MPa. Preferably, mass susceptibility of the alloy is not greater than $1.50 \times 10^{-6}$ cm$^3$/g.

In another aspect, the present invention is directed to a medical product in which a material of the medical product is an alloy that contains Zr as a main component, Nb the content of which is not less than 0.1% by weight and not greater than 25% by weight, Mo the content of which is not less than 0.1% by weight and not greater than 25% by weight, and Ta the content of which is not less than 0.1% by weight and not greater than 25% by weight, and that has a tensile strength of not less than 1000 MPa.

In still another aspect, a production method for producing an alloy according to the present invention includes: preparing a material that contains Zr as a main component, Nb the content of which is not less than 0.1% by weight and not greater than 25% by weight, Mo the content of which is not less than 0.1% by weight and not greater than 25% by weight, and Ta the content of which is not less than 0.1% by weight and not greater than 25% by weight; and subjecting the material to plastic working.

Preferably, the plastic working is swaging. Preferably, a reduction of area in the swaging is not less than 90%.

Preferably, the production method further includes subjecting the material to heat treatment after subjecting the material to the plastic working. Preferably, the heat treatment includes aging by heating, and quenching after the aging.

Advantageous Effects of the Invention

The alloy for biomedical use according to the present invention has low magnetic susceptibility. A medical product which does not easily cause an artifact can be obtained by the alloy. Furthermore, a medical product having excellent mechanical characteristics can be obtained by the alloy.

DESCRIPTION OF EMBODIMENTS

The following will describe in detail the present invention based on preferred embodiments with reference where appropriate to the accompanying drawing.

A material of a medical product according to the present invention is an alloy for biomedical use. The alloy for biomedical use contains Zr, Nb, Mo, and Ta. The remainder of the alloy is preferably unavoidable impurities.

The inventors of the present invention have examined a composition of a Zr-based alloy according to a d-electrons alloy design theory. The d-electrons alloy design theory is a method in which parameters representing characteristics of alloying elements are obtained and an alloy composition is examined by using the parameters. An alloy composition having target mechanical characteristics can be determined according to the theory.

Figure 1:
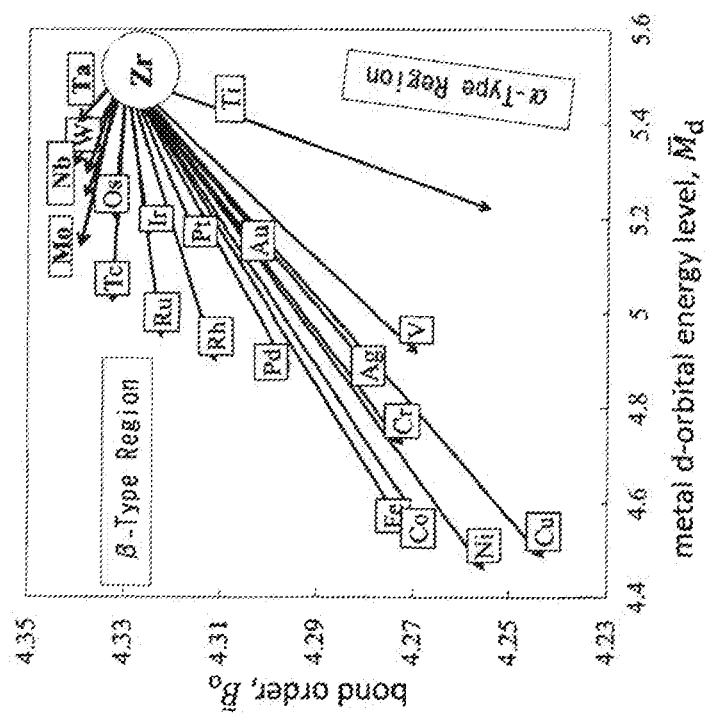
FIG. 1 shows a graph representing a result of examining a composition of a Zr-based alloy according to a d-electrons alloy design theory.

FIG. 1 shows a graph representing a result of examining a composition of a Zr-based alloy according to the d-electrons alloy design theory. In the graph, the directions indicated by arrows contribute to determination of phases, and the lengths of the arrows contribute to stability of the phases. The graph indicates that Nb, Mo, and Ta contribute to forming of a β-phase of a Zr alloy.

Zr is a main component of the alloy for biomedical use according to the present invention. The content of Zr is the greatest of elements contained in the alloy. Zr has low cytotoxicity. Furthermore, Zr has excellent corrosion resistance, and, therefore, a medical product using the alloy has excellent durability in an organism. The content of Zr in the alloy is preferably not less than 40% by weight and particularly preferably not less than 50% by weight.

Nb is a β-phase forming element. Nb contributes to reduction of the magnetic susceptibility of the alloy. The alloy can allow reduction of an artifact in MRI diagnosis. Nb and Zr can form a complete solid solution. Therefore, Nb can be uniformly distributed in the alloy. The alloy has excellent mechanical characteristics. Furthermore, Nb has low cytotoxicity.

The content of Nb in the alloy is preferably not less than 0.1% by weight and preferably not greater than 25% by weight. The alloy in which the content thereof is not less than 0.1% by weight can allow reduction of an artifact. Furthermore, the alloy in which the content thereof is not less than 0.1% by weight can contribute to mechanical characteristics of the medical product. From these viewpoints, the content thereof is more preferably not less than 0.5% by weight and particularly preferably not less than 12% by weight. The alloy in which the content thereof is not greater than 25% can allow reduction of an artifact. From this viewpoint, the content thereof is more preferably not greater than 20% by weight and particularly preferably not greater than 16% by weight.

Mo is a β-phase forming element. Mo contributes to reduction of the magnetic susceptibility of the alloy. The alloy can allow reduction of an artifact in MRI diagnosis. Mo contributes to mechanical characteristics of the alloy. Furthermore, Mo has low cytotoxicity.

The content of Mo in the alloy is preferably not less than 0.1% by weight and preferably not greater than 25% by weight. The alloy in which the content thereof is not less than 0.1% by weight can allow reduction of an artifact. Furthermore, the alloy in which the content thereof is not less than 0.1% by weight can contribute to mechanical characteristics of the medical product. From these viewpoints, the content thereof is more preferably not less than 0.8% by weight and particularly preferably not less than 1.0% by weight. The alloy in which the content thereof is not greater than 25% can allow reduction of an artifact. From this viewpoint, the content thereof is more preferably not greater than 10% by weight and particularly preferably not greater than 5% by weight.

Ta is a β-phase forming element. Ta also promotes forming of an ω-phase. Ta contributes to reduction of magnetic susceptibility of the alloy. The alloy can allow reduction of an artifact in MRI diagnosis. Ta and Zr can form a complete solid solution. Therefore, Ta can be uniformly distributed in the alloy. The alloy has excellent mechanical characteristics. Furthermore, Ta has low cytotoxicity.

The content of Ta in the alloy is preferably not less than 0.1% by weight and preferably not greater than 25% by weight. The alloy in which the content thereof is not less than 0.1% by weight can allow reduction of an artifact. Furthermore, the alloy in which the content thereof is not less than 0.1% by weight can contribute to mechanical characteristics of the medical product. From these viewpoints, the content thereof is more preferably not less than 1.0% by weight and particularly preferably not less than 3% by weight. The alloy in which the content thereof is not greater than 25% can allow reduction of an artifact. From this viewpoint, the content thereof is more preferably not greater than 15% by weight and particularly preferably not greater than 12% by weight.

The total content of Nb, Mo, and Ta in the alloy is preferably not less than 2% by weight and preferably not greater than 50% by weight. The alloy in which the total content is within the range can allow achievement of all of high tensile strength, great elongation at break, small Young's modulus, and low magnetic susceptibility. From this viewpoint, the total content is more preferably not less than 10% by weight and particularly preferably not less than 15% by weight. The total content is more preferably not greater than 40% by weight and particularly preferably not greater than 35% by weight.

According to the graph shown in FIG. 1, Mo makes a great contribution to stability of the β-phase and Ta makes a small contribution thereto. Therefore, a content PTa (% by weight) of Ta is preferably greater than a content PMo (% by weight) of Mo in the alloy. A ratio (PMo/PTa) is preferably not less than 1/20 and preferably not greater than 1/3, more preferably not less than 1/15 and more preferably not greater than 1/4, and particularly preferably not less than 1/10 and particularly preferably not greater than 1/5.

The alloy may contain a small amount of another element. Examples of the other element include B, C, N, O, Na, Mg, Si, P, S, K, Ca, and Mn. The total content of the other elements is preferably not greater than 10% by weight, more preferably not greater than 5% by weight, and particularly preferably not greater than 1.0% by weight.

The magnetic susceptibility (mass susceptibility) of the alloy is preferably not greater than $1.50 \times 10^{-6}$ cm$^3$/g. The alloy in which the magnetic susceptibility is within this range can allow reduction of an artifact. From this viewpoint, the magnetic susceptibility is more preferably not greater than $1.45 \times 10^{-6}$ cm$^3$/g and particularly preferably not greater than $1.40 \times 10^{-6}$ cm$^3$/g. The magnetic susceptibility is measured by using a cylindrical test piece. In the test piece, the diameter of the bottom surface is 3 mm and the height is 25 mm. The measurement is performed by using a manually-operated magnetic balance ("MSK-MKI" manufactured by Sherwood Scientific). The applied magnetic field is 0.35T.

The Young's modulus of the alloy is preferably not greater than 100 GPa. When a fixation member for a broken bone, an artificial joint stem, and the like are obtained by using the alloy having the Young's modulus in this range, bone resorption due to stress shielding can be reduced. From this viewpoint, the Young's modulus is more preferably not greater than 80 GPa and particularly preferably not greater than 70 GPa. The Young's modulus is preferably not less than 10 GPa and particularly preferably not less than 20 GPa. A cylindrical test piece is used for measuring the Young's modulus. In the test piece, the diameter of the bottom surface is 3 mm and the height is 52 mm. The measurement is performed by using an automatic resonant-type elastic modulus measurement device ("JE-RT" manufactured by Nihon Techno-Plus Corp.) in compliance with the standard of "JIS Z 2280".

Figure 2:
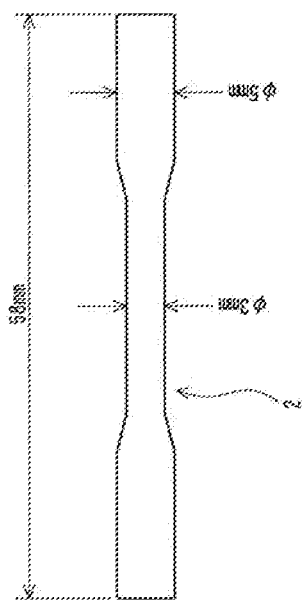
FIG. 2 is a front view of a test piece used for a tensile test.

The tensile strength of the alloy is not less than 1000 MPa. A medical product having excellent durability can be obtained from the alloy in which the tensile strength is not less than 1000 MPa. From this viewpoint, the tensile strength is more preferably not less than 1030 MPa and particularly preferably not less than 1060 MPa. The tensile strength is measured by a tensile test. For the tensile test, a test piece 2 having the shape shown in FIG. 2 is used. The test piece 2 is obtained by an argon arc centrifugal casting method. In this casting method, the internal pressure in a chamber is adjusted to be not higher than $1.2 \times 10^{-1}$ Pa, and argon gas having a purity of not less than 99.9% is thereafter injected into the chamber, and the internal pressure is adjusted to 0.06 MPa. In the chamber, the casting is performed. The tensile test is performed by using a precision universal tester ("AG-2000B" manufactured by SHIMADZU CORPORATION) in compliance with the standard of "JIS Z 2241". The initial strain rate is $1.3 \times 10^{-3}$ at the test.

The 0.2% proof stress of the alloy is preferably not less than 900 MPa. A medical product having excellent durability can be obtained from the alloy in which the 0.2% proof stress is not less than 900 MPa. From this viewpoint, the 0.2% proof stress is more preferably not less than 950 MPa and particularly preferably not less than 1000 MPa. The 0.2% proof stress is measured by the tensile test described above.

The elongation at break is preferably not less than 5% in the alloy. A medical product having excellent durability can be obtained from the alloy in which the elongation at break is not less than 5%. From this viewpoint, the elongation at break is more preferably not less than 8% and particularly preferably not less than 10%. The elongation at break is measured by the tensile test described above.

Figure 3:
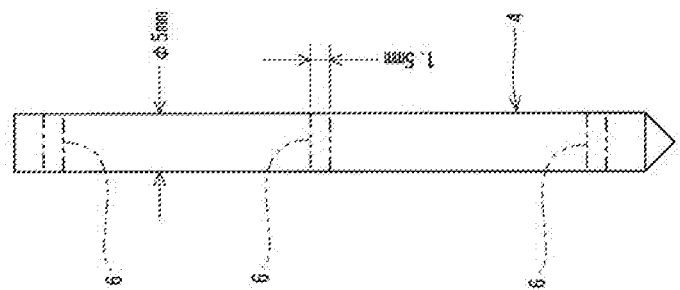
FIG. 3 is a front view of an ingot used for measuring a Vickers hardness.

The Vickers hardness of the alloy is preferably not less than 250. A medical product having excellent durability can be obtained from the alloy in which the Vickers hardness is not less than 250. From this viewpoint, the Vickers hardness is particularly preferably not less than 400. When the Vickers hardness is measured, three disks 6 each having the height of 1.5 mm are cut out from an ingot 4 having the shape shown in FIG. 3. The Vickers hardness is measured on the cross-section of each disk 6 in compliance with the standard of "JIS Z 2244". The measurement is performed at randomly selected 12 points, and the results at the 12 points are averaged. The load is 3N at the measurement. The retention time is 15 seconds at the measurement.

The medical product according to the present invention includes a biomedical implant and a medical device. Examples of the biomedical implant include implants such as an artificial bone, an artificial tooth root, and an artificial joint. Examples of the other biomedical implants include a bone fixing plate, an osteosynthesis nail, an osteosynthesis screw, an intramedullary nail, a ligator (for example, clip), a suturing device (for example, stapler), an artificial joint, a blood vessel repairer (for example, stent), and an artificial heart valve. Even when MRI diagnosis is performed for patients who have these biomedical implants, an artifact does not easily occur in an image.

Examples of the medical device include surgical instruments such as a medical knife, medical scissors, medical tweezers, a medical spoon, a medical hook, medical forceps, a medical saw, a medical chisel, a medical elevatorium, a medical mallet, a file for medical use, a medical lever, a medical snare, an injection needle, a puncture needle, a medical lancet, a drill, a perforator, a medical beaked tube (for example, catheter guide wire), and a body fluid guiding tube. In MRI diagnosis with the use of these medical devices, an artifact does not easily occur in an image.

Figure 4:
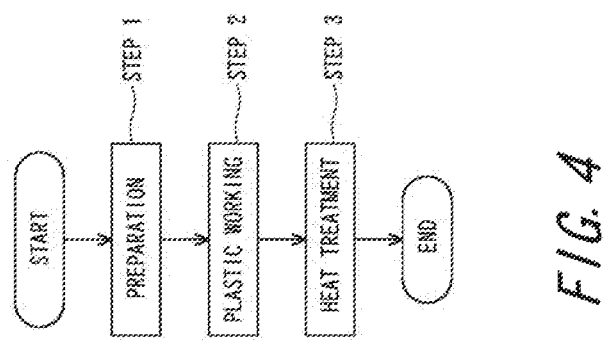
FIG. 4 is a flow chart showing a production method for producing an alloy for biomedical use according to one embodiment of the present invention.

FIG. 4 is a flow chart showing an example of a production method for producing the alloy for biomedical use. In the production method, a material is firstly prepared (STEP1). The composition of the material is the same as the composition of the alloy for biomedical use. The material is typically obtained by casting.

The material is subjected to plastic working (STEP2). The plastic working enables the material to be formed into a desired shape. The plastic working may be hot plastic working or cold plastic working. Examples of the plastic working include forging, swaging, drawing, and extruding.

The material is subjected to heat treatment (STEP3). The heat treatment is typically aging treatment. In the aging treatment, the material is maintained at a high temperature. By the material being thus maintained, the elements are formed into a matrix as a solid solution. The material is quenched and the alloy for biomedical use is obtained.

By the plastic working and the heat treatment, the material is hardened. By the hardening, an alloy having a high tensile strength can be obtained. When the material is sufficiently hardened merely by the plastic working, the heat treatment may be omitted.

The plastic working is preferably cold swaging. In the swaging, the material passes between a pair of dies. The interval between the dies is periodically changed, whereby the material is struck by the dies. Thus, the diameter of the material is reduced. When the reduction of area is not less than 90% in the swaging, an alloy having the tensile strength of not less than 1000 MPa can be obtained. The reduction P of area can be calculated according to the following equation.

$$P=((So-S)/So)*100$$

In the equation, So represents a cross-sectional area of the material before the swaging, and S represents a cross-sectional area of the material after the swaging. These cross-sectional areas are measured on a cross-section along the surface perpendicular to the material advancing direction.

Figure 5:
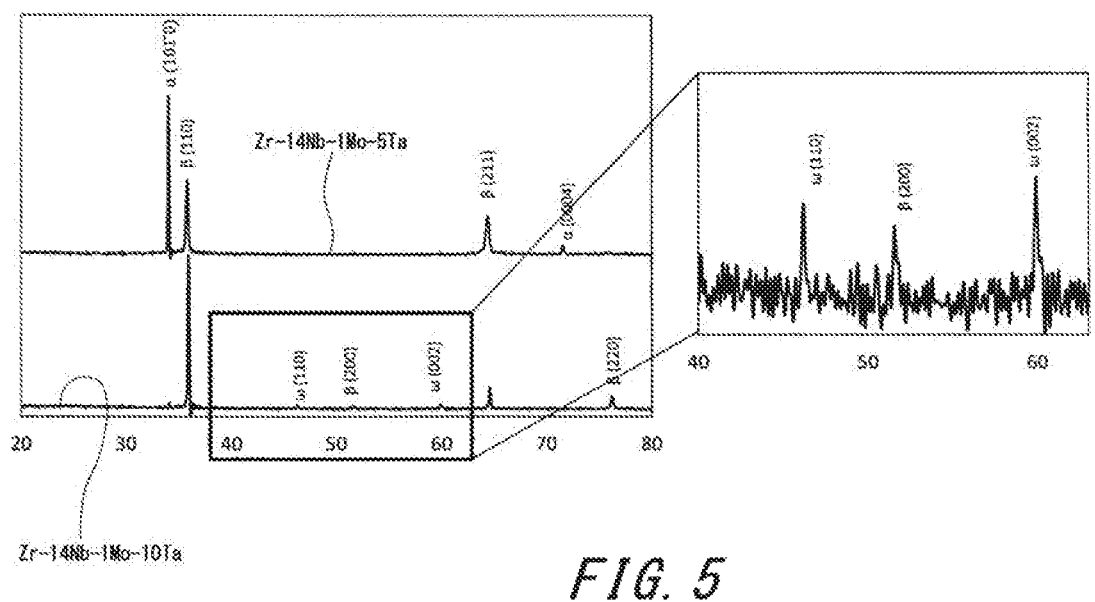
FIG. 5 shows a graph representing results of XRD.

Specific examples of the alloy according to the present invention include Zr-14Nb-1Mo-5Ta and Zr-14Nb-1Mo-10Ta. FIG. 5 shows a graph representing the results of the XRD of these alloys. The graph indicates that the α-phase and the β-phase are formed by precipitation for Zr-14Nb-1Mo-5Ta. The graph indicates that the α-phase, the β-phase, and the ω-phase are formed by precipitation for Zr-14Nb-1Mo-10Ta. The graph indicates that the α-phase is reduced, the β-phase is increased, and the ω-phase is increased according to the increase of the content of Ta.

EXAMPLES

The following will show the effects of the present invention by means of examples, but the present invention should not be construed in a limited manner based on the description of these examples.

Experiment 1

Example 1

A material was obtained by induction skull melting and casting. The composition of the material was Zr-14Nb-1Mo-5Ta. The material was heated to 1300° C., and was then subjected to forging. The material was retained for 45 minutes at the temperature of 400° C. in a vacuum environment. The material was immersed in ice water and quenched, and the alloy, for biomedical use, of example 1 was obtained.

Comparative Example 1

An alloy, for biomedical use, of comparative example 1 was obtained in the same manner as in example 1 except that the material was not subjected to forging and heat treatment.

Comparative Example 2

An alloy, for biomedical use, of comparative example 2 was obtained in the same manner as in example 1 except that the material was not subjected to heat treatment.

Comparative Examples 3 to 10

Materials having compositions indicated below in Tables 2 and 3 were prepared, and the materials were not subjected to plastic working and heat treatment. Thus, alloys, for biomedical use, of comparative examples 3 to 10 were obtained.

[Evaluation]

The Vickers hardness, tensile strength, 0.2% proof stress, elongation at break, Young's modulus, and mass susceptibility were measured in the above-described methods. The results are indicated below in Tables 1 to 3.

TABLE 1

Results of experiment 1

|  | Comp. Ex. 1 | Comp. Ex. 2 | Example 1 |
|---|---|---|---|
| Composition | Zr—14Nb—1Mo—5Ta | Zr—14Nb—1Mo—5Ta | Zr—14Nb—1Mo—5Ta |
| Status | Before processing | After forging | After heat treatment |
| Vickers hardness | 208 | 213 | 261 |
| Tensile strength (MPa) | 796 | 650 | 1033 |
| 0.2% proof stress (MPa) | 754 | 629 | 986 |
| Elongation at break (%) | 15 | 17 | 9 |
| Young's modulus (GPa) | 61 | 64 | 68 |
| Magnetic susceptibility ($\times 10^{-6}$ cm$^3$/g) | 1.38 | 1.39 | 1.34 |

TABLE 2

Results of experiment 1

|  | Comp. Ex. 3 | Comp. Ex. 4 | Comp. Ex. 5 | Comp. Ex. 6 |
|---|---|---|---|---|
| Composition | Zr—14Nb—1Mo—10Ta | pure Zr | Zr—14Nb | Zr—1Mo |
| Status | Before processing | Before processing | Before processing | Before processing |
| Vickers hardness | 210 | 129 | 275 | 203 |
| Tensile strength (MPa) | 765 | 451 | 784 | 970 |
| 0.2% proof stress (MPa) | 717 | 349 | 686 | 855 |
| Elongation at break (%) | 11 | 13.7 | 12 | 2.9 |
| Young's modulus (GPa) | 58 | 95 | 70 | 98 |
| Magnetic susceptibility ($\times 10^{-6}$ cm$^3$/g) | 1.35 | 1.34 | 1.35 | 1.13 |

TABLE 3

Results of experiment 1

|  | Comp. Ex. 7 | Comp. Ex. 8 | Comp. Ex. 9 | Comp. Ex. 10 |
|---|---|---|---|---|
| Composition | Ti | Ti—6Al—4V ELI | Ti—6Al—7Nb | Co—Cr—Mo |
| Status | Before processing | Before processing | Before processing | Before processing |
| Vickers hardness | 168 | 320 | 315 | 345 |
| Tensile strength (MPa) | — | 980 | 933 | 980 |

TABLE 3-continued

Results of experiment 1

|  | Comp. Ex. 7 | Comp. Ex. 8 | Comp. Ex. 9 | Comp. Ex. 10 |
|---|---|---|---|---|
| 0.2% proof stress (MPa) | — | 920 | 817 | 680 |
| Elongation at break (%) | — | 14 | 7 | 11 |
| Young's modulus (GPa) | 100 | 100 | 114 | 200 |
| Magnetic susceptibility ($\times 10^{-6}$ cm$^3$/g) | 2.90 | 3.17 | 2.81 | 7.52 |

As indicated in Tables 1 to 3, the alloy for biomedical use according to example had excellent performances.

Experiment 2

Example 2

A material was obtained by induction skull melting and casting. The composition of the material was Zr-14Nb-1Mo-5Ta. The material was subjected to cold swaging. The reduction of area in the swaging was 57%. The material was retained for 45 minutes at the temperature of 400° C. in a vacuum environment. The material was immersed in ice water and quenched, and the alloy, for biomedical use, of example 2 was obtained.

Comparative Example 11

An alloy, for biomedical use, of comparative example 11 was obtained in the same manner as in example 2 except that the material was not subjected to heat treatment.

[Evaluation]

The Vickers hardness, Young's modulus, and mass susceptibility were measured in the above-described methods. The results are indicated below in Tables 4 to 6.

TABLE 4

Results of experiment 2

|  | Comp. Ex. 1 | Comp. Ex. 11 | Example 2 |
|---|---|---|---|
| Composition | Zr—14Nb—1Mo—5Ta | Zr—14Nb—1Mo—5Ta | Zr—14Nb—1Mo—5Ta |
| Status | Before processing | After swaging | After heat treatment |
| Vickers hardness | 208 | 239 | 402 |
| Young's modulus (GPa) | 61 | 66 | 89 |
| Magnetic susceptibility ($\times 10^{-6}$ cm$^3$/g) | 1.38 | 1.35 | 1.21 |

TABLE 5

Results of experiment 2

|  | Comp. Ex. 3 | Comp. Ex. 4 | Comp. Ex. 5 | Comp. Ex. 6 |
|---|---|---|---|---|
| Composition | Zr—14Nb—1Mo—10Ta | pure Zr | Zr—14Nb | Zr—1Mo |
| Status | Before processing | Before processing | Before processing | Before processing |
| Vickers hardness | 210 | 129 | 275 | 203 |
| Young's modulus (GPa) | 58 | 95 | 70 | 98 |
| Magnetic susceptibility ($\times 10^{-6}$ cm$^3$/g) | 1.35 | 1.34 | 1.35 | 1.13 |

TABLE 6

Results of experiment 2

|  | Comp. Ex. 7 | Comp. Ex. 8 | Comp. Ex. 9 | Comp. Ex. 10 |
|---|---|---|---|---|
| Composition | Ti | Ti—6Al—4V ELI | Ti—6Al—7Nb | Co—Cr—Mo |
| Status | Before processing | Before processing | Before processing | Before processing |
| Vickers hardness | 168 | 320 | 315 | 345 |
| Young's modulus (GPa) | 100 | 100 | 114 | 200 |
| Magnetic susceptibility ($\times 10^{-6}$ cm$^3$/g) | 2.90 | 3.17 | 2.81 | 7.52 |

As indicated in Tables 4 to 6, the alloy for biomedical use according to example had excellent performances.

Experiment 3

Example 3

A material was obtained by induction skull melting and casting. The composition of the material was Zr-14Nb-1Mo-5Ta. The material was subjected to cold swaging. The reduction of area in the swaging was 97%. The material was retained for 45 minutes at the temperature of 400° C. in a vacuum environment. The material was immersed in ice water and quenched, and the alloy, for biomedical use, of example 3 was obtained.

Example 4

An alloy, for biomedical use, of example 4 was obtained in the same manner as in example 3 except that the material was not subjected to heat treatment.

[Evaluation]

The Vickers hardness, tensile strength, 0.2% proof stress, elongation at break, Young's modulus, and mass susceptibility were measured in the above-described methods. The results are indicated below in Tables 7 to 9.

TABLE 7

|  | Comp. Ex. 1 | Example 4 | Example 3 |
| --- | --- | --- | --- |
| Composition | Zr—14Nb—1Mo—5Ta | Zr—14Nb—1Mo—5Ta | Zr—14Nb—1Mo—5Ta |
| Status | Before processing | After swaging | After heat treatment |
| Vickers hardness | 208 | 260 | 433 |
| Tensile strength (MPa) | 796 | 1066 | 1661 |
| 0.2% proof stress (MPa) | 754 | 1008 | — |
| Elongation at break (%) | 15 | 14 | 1 |
| Young's modulus (GPa) | 61 | 67 | 97 |
| Magnetic susceptibility ($\times 10^{-6}$ cm$^3$/g) | 1.38 | 1.34 | 1.28 |

TABLE 8

| Results of experiment 3 | | | | |
| --- | --- | --- | --- | --- |
|  | Comp. Ex. 3 | Comp. Ex. 4 | Comp. Ex. 5 | Comp. Ex. 6 |
| Composition | Zr-14Nb-1Mo-10Ta | pure Zr | Zr-14Nb | Zr-1Mo |
| Status | Before processing | Before processing | Before processing | Before processing |
| Vickers hardness | 210 | 129 | 275 | 203 |
| Tensile strength (MPa) | 765 | 451 | 784 | 970 |
| 0.2% proof stress (MPa) | 717 | 349 | 686 | 855 |
| Elongation at break (%) | 11 | 13.7 | 12 | 2.9 |
| Young's modulus (GPa) | 58 | 95 | 70 | 98 |
| Magnetic susceptibility ($\times 10^{-6}$ cm$^3$/g) | 1.35 | 1.34 | 1.35 | 1.13 |

TABLE 9

| Results of experiment 3 | | | | |
| --- | --- | --- | --- | --- |
|  | Comp. Ex. 7 | Comp. Ex. 8 | Comp. Ex. 9 | Comp. Ex. 10 |
| Composition | Ti | Ti—6Al—4V ELI | Ti—6Al—7Nb | Co—Cr—Mo |
| Status | Before processing | Before processing | Before processing | Before processing |
| Vickers hardness | 168 | 320 | 315 | 345 |
| Tensile strength (MPa) | — | 980 | 933 | 980 |
| 0.2% proof stress (MPa) | — | 920 | 817 | 680 |
| Elongation at break (%) | — | 14 | 7 | 11 |
| Young's modulus (GPa) | 100 | 100 | 114 | 200 |
| Magnetic susceptibility ($\times 10^{-6}$ cm$^3$/g) | 2.90 | 3.17 | 2.81 | 7.52 |

As indicated in Tables 7 to 9, the alloy for biomedical use according to each example had excellent performances.

Experiment 4

Example 5

A material was obtained by induction skull melting and casting. The composition of the material was Zr-14Nb-1Mo-5Ta. The material was subjected to plastic working, to obtain a linear base material having a diameter of 3.1 mm. The base material was annealed. The base material was subjected to drawing process with the use of dies, and the alloy for biomedical use according to example 5 in which the diameter was 2.05 mm was obtained. The degree of the process in the drawing process was 57%.

Example 6

An alloy for biomedical use according to example 6 in which the diameter was 0.53 mm was obtained by further subjecting the alloy of example 5 to the drawing process with the use of the dies. The degree of process in the drawing process was 97%.

[Evaluation]

The Vickers hardness, tensile strength, 0.2% proof stress, elongation at break, Young's modulus, and mass susceptibility were measured in the above-described methods. The results are indicated below in Table 10. A wire material obtained by the drawing process was used as it was in the tensile test without shaving the wire material, and the tensile strength, 0.2% proof stress, and elongation at break were measured. For the tensile test, AG-20 kN manufactured by SHIMADZU CORPORATION was used.

TABLE 10

Results of experiment 4

| | Example 5 | Example 6 |
|---|---|---|
| Composition | Zr—14Nb—1Mo—5Ta | Zr—14Nb—1Mo—5Ta |
| Status | Drawing with dies 57% | Drawing with dies 97% |
| Vickers hardness | 232 | 262 |
| Tensile strength (MPa) | 898 | 1018 |
| 0.2% proof stress (MPa) | 714 | 896 |
| Elongation at break (%) | 14.3 | 4.8 |
| Young's modulus (GPa) | — | — |
| Magnetic susceptibility ($\times 10^{-6}$ cm$^3$/g) | 1.51 | 1.52 |

As indicated in Table 10, the alloy for biomedical use according to each example had excellent performances.

The evaluation results of experiments 1 to 4 clearly indicate that the present invention is superior.

INDUSTRIAL APPLICABILITY

The alloy according to the present invention is suitable for various objects applied to organisms in MRI diagnosis.

DESCRIPTION OF THE REFERENCE CHARACTERS

2 . . . test piece for tensile test
4 . . . ingot used for measuring Vickers hardness
6 . . . disk used for measuring Vickers hardness

The invention claimed is:

1. An alloy for biomedical use, the alloy consisting of:
Zr as a main component, Nb the content of which is not less than 0.1% by weight and not greater than 25% by weight, Mo the content of which is not less than 0.1% by weight and not greater than 25% by weight, Ta the content of which is not less than 0.1% by weight and not greater than 25% by weight, and unavoidable impurities, wherein
a tensile strength of the alloy is not less than 1000 MPa, and
a ratio (PMo/PTa) of a content PTa (% by weight) of Ta to a content PMo (% by weight) of Mo is not less than 1/20 and not greater than 1/3.

2. The alloy, for biomedical use, according to claim 1, wherein a total content of Nb, Mo, and Ta is not less than 2% by weight and not greater than 50% by weight.

3. The alloy, for biomedical use, according to claim 1, wherein a 0.2% proof stress of the alloy is not less than 900 MPa.

4. The alloy, for biomedical use, according to claim 1, wherein mass susceptibility of the alloy is not greater than $1.50 \times 10^{-6}$ cm$^3$/g.

5. The alloy for biomedical use, according to claim 1, the alloy contains Zr in an amount of at least 80% by weight, Nb the content of which is not less than 0.1% by weight and not greater than 16% by weight, Mo the content of which is not less than 0.1% by weight and not greater than 10% by weight, Ta the content of which is not less than 0.1% by weight and not greater than 15% by weight.

6. A production method for producing the alloy for biomedical use according to claim 1, the production method comprising:
preparing a material that contains Zr as a main component, Nb the content of which is not less than 0.1% by weight and not greater than 25% by weight, Mo the content of which is not less than 0.1% by weight and not greater than 25% by weight, and Ta the content of which is not less than 0.1% by weight and not greater than 25% by weight; and
subjecting the material to plastic working.

7. The production method according to claim 6, wherein the plastic working is swaging, and
a reduction of area in the swaging is not less than 90%.

8. The production method according to claim 6, further comprising
subjecting the material to heat treatment after subjecting the material to the plastic working.

9. The production method according to claim 8, wherein the heat treatment includes aging by heating, and quenching after the aging.

10. A medical product, wherein
a material of the medical product is an alloy that contains Zr as a main component, Nb the content of which is not less than 0.1% by weight and not greater than 25% by weight, Mo the content of which is not less than 0.1% by weight and not greater than 25% by weight, Ta the content of which is not less than 0.1% by weight and not greater than 25% by weight, and that has a tensile strength of not less than 1000 MPa, and a ratio (PMo/PTa) of a content PTa (% by weight) of Ta to a content PMo (% by weight) of Mo is not less than 1/20 and not greater than 1/3.

11. An alloy for biomedical use, the alloy consisting of:
Zr as a main component in an amount of at least 80% by weight, Nb the content of which is not less than 0.1% by weight and not greater than 16% by weight, Mo the content of which is not less than 0.1% by weight and not greater than 10% by weight, Ta the content of which is not less than 0.1% by weight and not greater than 15% by weight, and unavoidable impurities, wherein
a tensile strength of the alloy is not less than 1000 MPa.

12. A medical product, wherein
a material of the medical product is an alloy that contains Zr as a main component in an amount of at least 80% by weight, Nb the content of which is not less than 0.1% by weight and not greater than 16% by weight, Mo the content of which is not less than 0.1% by weight and not greater than 10% by weight, Ta the content of which is not less than 0.1% by weight and not greater than 15% by weight, and that has a tensile strength of not less than 1000 MPa.

* * * * *